United States Patent
Hahnen et al.

[11] Patent Number: 5,908,419
[45] Date of Patent: Jun. 1, 1999

[54] RESECTOSCOPE ROLLER ELECTRODE HAVING HIGH HEAT ZONE INSERT

[75] Inventors: Kevin F. Hahnen, Pleasanton, Calif.; Boris Kesler, Hialeah, Fla.

[73] Assignee: Symbiosis Corporation, Miami, Fla.

[21] Appl. No.: 08/794,997

[22] Filed: Feb. 5, 1997

[51] Int. Cl.[6] .................................................. A61B 17/39
[52] U.S. Cl. ................................ 606/46; 606/49; 606/147
[58] Field of Search .............................. 606/41, 45, 46, 606/49; 601/20; 607/147; 219/233

[56] References Cited

U.S. PATENT DOCUMENTS

| | | | |
|---|---|---|---|
| 1,930,214 | 10/1933 | Wappler | 174/89 |
| 1,963,636 | 6/1934 | Wappler | 174/89 |
| 1,971,024 | 8/1934 | Wappler | 174/89 |
| 2,002,594 | 5/1935 | Wappler et al. | 174/89 |
| 2,004,559 | 6/1935 | Wappler et al. | 174/89 |
| 2,011,169 | 8/1935 | Wappler | 174/89 |
| 2,090,923 | 8/1937 | Wappler | 128/303.15 |
| 2,224,464 | 12/1940 | Wolf | 128/303.14 |
| 2,487,502 | 11/1949 | Willinsky | 128/303.14 |
| 2,558,192 | 6/1951 | Nockunas | 219/233 |
| 2,815,757 | 12/1957 | Piar | 128/303.14 |
| 3,149,633 | 9/1964 | Zingale | 128/303.15 |
| 3,752,159 | 8/1973 | Wappler | 128/303.15 |
| 3,856,015 | 12/1974 | Iglesias | 128/303.15 |
| 3,939,839 | 2/1976 | Curtiss | 128/303.15 |
| 3,973,568 | 8/1976 | Iglesias | 128/303.15 |
| 3,990,456 | 11/1976 | Iglesias | 128/303.15 |
| 4,030,502 | 6/1977 | Iglesias | 128/303.15 |
| 4,134,406 | 1/1979 | Iglesias | 128/303.15 |
| 4,149,538 | 4/1979 | Mrava et al. | 128/303.15 |
| 4,362,160 | 12/1982 | Hiltebrandt | 128/303.15 |
| 4,506,668 | 3/1985 | König | 128/303.15 |
| 4,649,917 | 3/1987 | Karasawa | 128/303.14 |
| 4,657,018 | 4/1987 | Hakky | 128/303.15 |
| 4,726,370 | 2/1988 | Karasawa et al. | 128/303.15 |
| 4,917,082 | 4/1990 | Grossi et al. | 606/46 |
| 5,007,907 | 4/1991 | Nishigaki et al. | 606/46 |
| 5,064,424 | 11/1991 | Bitrolf | 606/46 |
| 5,088,998 | 2/1992 | Sakashita et al. | 606/46 |
| 5,196,011 | 3/1993 | Korth et al. | 606/46 |
| 5,201,741 | 4/1993 | Dulebohn | 606/113 |
| 5,318,564 | 6/1994 | Eggers | 606/47 |
| 5,324,288 | 6/1994 | Billings et al. | 606/45 |
| 5,342,357 | 8/1994 | Nardella | 606/40 |
| 5,354,296 | 10/1994 | Turkel | 606/41 |
| 5,374,188 | 12/1994 | Frank et al. | 433/32 |
| 5,376,087 | 12/1994 | Haber et al. | 606/27 |
| 5,395,312 | 3/1995 | Desai | 604/22 |
| 5,395,363 | 3/1995 | Billings et al. | 606/45 |
| 5,395,368 | 3/1995 | Ellman et al. | 606/45 |
| 5,599,349 | 2/1997 | D'Amelio | 606/46 |
| 5,669,906 | 9/1997 | Grossi et al. | 606/46 |

FOREIGN PATENT DOCUMENTS

| | | | |
|---|---|---|---|
| 2 222 820 | 11/1973 | Germany . | |
| 3707-403 | 9/1987 | Germany | 606/46 |
| 195 14 552 A1 | 10/1996 | Germany . | |
| WO 97/07747 | 3/1997 | WIPO . | |
| WO 97/49346 | 12/1997 | WIPO . | |

*Primary Examiner*—Lee Cohen
*Attorney, Agent, or Firm*—Testa, Hurwitz & Thibeault, LLP

[57] ABSTRACT

An electrocautery probe includes a pair of arms between which a roller electrode is rotatably mounted. The arms are joined at their proximal ends to an electrode lead and a mounting sleeve is provided intermediate of the arms and the lead for slideably coupling the probe to a resectoscope. According to one aspect of the invention, the roller electrode includes a cylindrical member having a central bore and an outer surface, and an insert extending longitudinally through the central bore. Preferably the cylindrical member is made of a first conductive material and the insert is made of a second conductive material. The insert has a plurality of corners and an axial bore. The roller electrode is preferably made of stainless steel, while the insert is preferably made of copper or tungsten. The outer diameter of the roller electrode is preferably approximately 0.120 inches, while the wall of the distance from at least on of the corners of the insert to the outer surface of cylindrical member is preferably approximately 0.005 inches thick. The cross-section of the central bore and the insert may similarly define any polygonal or other shape having corners. It has been discovered that the corners of the insert focus the cautery energy through the roller electrode to provide high heat zones for enhanced tissue vaporization.

25 Claims, 5 Drawing Sheets

RESECTOSCOPE ROLLER ELECTRODE HAVING HIGH HEAT ZONE INSERT

BACKGROUND OF THE INVENTION

1. Field of the Invention

This invention relates broadly to surgical instruments. More particularly, this invention relates to electrodes for resectoscopes.

2. State of the Art

Electrosurgical resection is a procedure in which damaged or enlarged tissue is excised with an electrocautery probe. Transurethral resection is an electrosurgical procedure in which a portion of the prostrate is excised by means of an instrument passed through the urethra. Endometrial ablation is an electrosurgical alternative procedure to hysterectomy for women with menorrhagia (abnormal or excessive uterine bleeding). In these procedures, the instrument typically used is called a resectoscope or hysteroscope. Prior art FIG. 1 shows a typical resectoscope 10 with an electrocautery probe 12. The resectoscope 10 includes a distal guide tube 14 and a proximal handle 16. A telescope 18 is inserted through the guide tube 14 and is provided with a proximal eye piece 20 for viewing the interior of the bladder or other operative site. The cautery probe 12 has a distal electrode 22 which is mounted between a pair of arms 23, 25. The arms 23, 25 are joined at their proximal ends to an electrode lead 27 which is coupled via the handle 16 to a wire 24 which is coupled to a source of cautery current (not shown). A mounting sleeve 29 is provided on the probe 12 for slideably coupling it to the guide tube 14. The mounting sleeve 29 is typically located at the point where the arms 23, 25 are joined to the electrode lead 27. The handle 16 is generally capable of axially sliding the probe 12 and its distally mounted electrode 22 relative to the guide tube 14.

The ablation or resection procedure involves applying a cauterizing voltage to the electrode 22 and moving the electrode slowly over the prostate or endometrium while viewing the tissue through the scope 18. Thermal and/or electrical energy is applied through the electrode to the prostate or the endometrium so that tissue is excised or ablated. The resectoscope and cautery probe are also useful in other procedures for resecting the uterus, ureter, or renal pelvis.

Known electrodes for use in resectoscope are available in many different shapes and sizes. U.S. Pat. No. 4,917,082 to Grossi et al., for example, discloses several embodiments of a resectoscope electrodes including a coagulating electrode, a knife electrode, a punctate electrode, and a roller electrode, among others. Electrodes for use with resectoscope are also widely available from Olsen Electrosurgical, Inc., Concord, Calif. They are available as blades, needles, balls, loops, spear tips, flexible wires, semi-circular wires, hooks, spatulas and blunt tips.

Recently, the generally preferred electrode for use in endometrial ablation is the roller (often referred to as "roller bar" or "roller ball") electrode. Prior art FIGS. 1 and 2 show a roller bar electrode 22. The roller bar is approximately 2.5 mm long and has a central bore 22b. It is rotatably mounted between the arms 23, 25 at the distal end of the electrocautery probe 12 by means of an axle wire 21 which extends through the central bore 22b of the electrode 22. The roller bar is supplied with a cauterizing voltage through the wire 21 which is coupled to the arms 23, 25 in the probe 12. When energized, the electrode 22 is rolled across the endometrial surface methodically until desired areas of the endometrium have been ablated. Roller bar electrodes are also used in prostatic resection. A substantially rounded roller bar is preferred because the shape provides a larger surface area which allows the electrode to cover more tissue and thereby shorten the procedure. It is also understood that in the case of prostatic resection, the overall size of the electrode, as well as the resectoscope must be kept to a minimum. It is preferred that in both endometrial ablation and prostatic resection that the roller electrode have high heat zones for enhanced tissue vaporization. One manner of introducing high heat zones into an electrode is to create grooves in the electrode. For example, co-owned U.S. Ser. No. 08/425,363 discloses several embodiments of a roller electrode having an outer surface which is provided with a plurality of longitudinal grooves. The longitudinal grooves define relatively sharp edges which serve to create high heat zones. However, tissue tends to accumulate in the grooves and on the surface of the electrode and interfere with the surgical procedure.

SUMMARY OF THE INVENTION

It is therefore an object of the invention to provide an electrocautery probe having an electrode with a maximized surface area.

It is another object of the invention to provide an electrocautery probe having an electrode with high heat zones for better tissue vaporization.

It is also an object of the invention to provide an electrocautery probe having an electrode with a relatively small overall size.

In accord with these objects which will be discussed in detail below, the electrocautery probe of the present invention includes a pair of arms between which a roller electrode is rotatably mounted. The arms are joined at their proximal ends to an electrode lead and a mounting sleeve is provided intermediate of the arms and the lead for slideably coupling the probe to a resectoscope. The roller electrode includes a cylindrical member having a central bore and an outer surface. An insert having a plurality of corners and an axial bore extends longitudinally through the central bore. The cylindrical member is made of a first conductive material and the insert is made of a second conductive material.

The roller electrode according to the invention is preferably made of stainless steel, while the insert is preferably made of copper or tungsten. The diameter of the roller electrode is preferably approximately 0.120 inches, while the distance from a corner of the insert to the outer surface of the roller electrode is preferably approximately 0.005 inches. Preferably the central bore has a rectangular cross-section and the insert has substantially the same cross-section as the central bore; i.e. the insert has four corners. It will be appreciated that the cross-sections of the central bore and the insert may have any polygonal or other shape having corners. It has been discovered that the corners of the insert focus the cautery energy through the cylindrical member to provide an electrode producing high heat zones for enhanced tissue vaporization.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
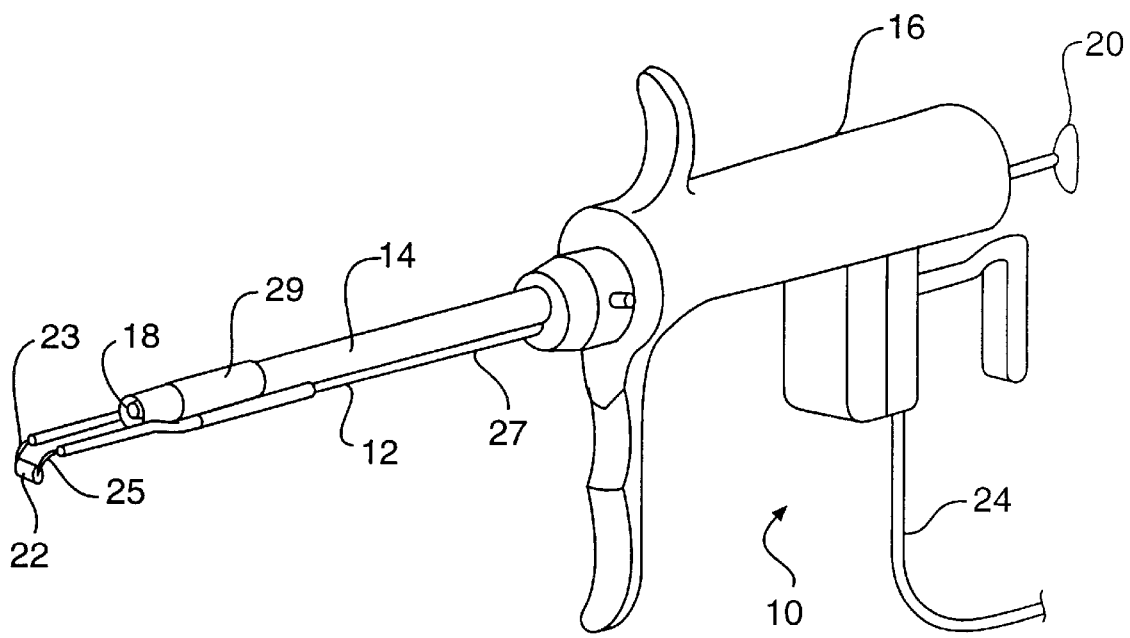
FIG. 1 is perspective view of a prior art resectoscope with an electrocautery probe having a roller bar electrode.
Figure 2:
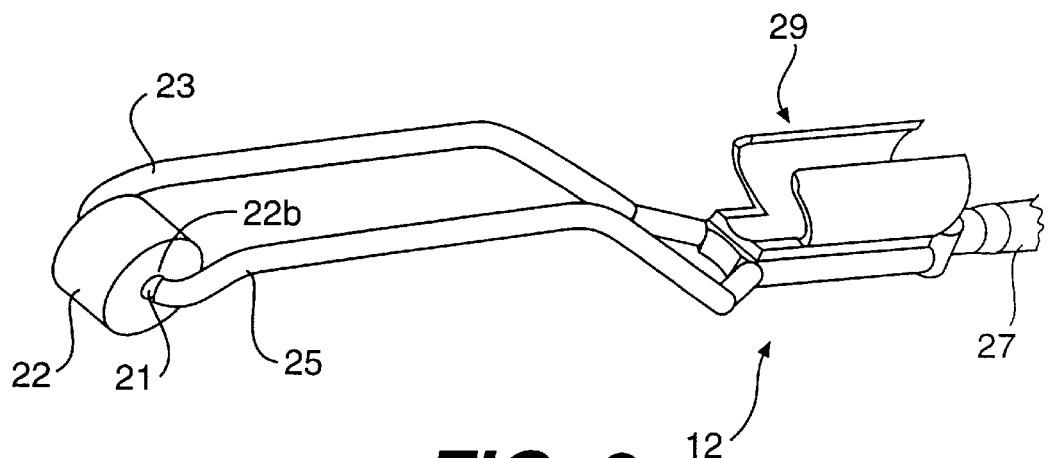
FIG. 2 is an enlarged broken perspective view of the distal end of the prior art electrocautery probe of FIG. 1.
Figure 3:
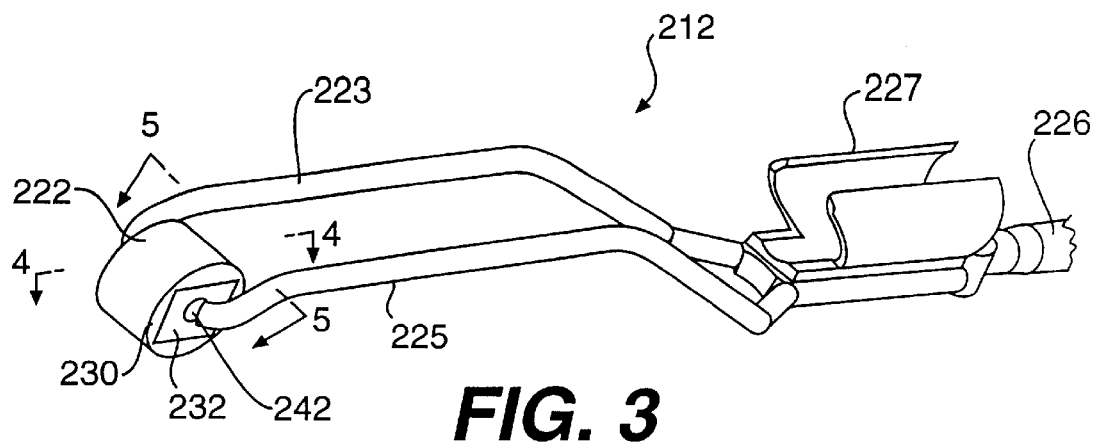
FIG. 3 is an enlarged broken perspective view of the distal end of an electrocautery probe having a roller electrode according to a first embodiment of the invention.

Referring now to FIG. 3, an electrocautery probe 212 according to the invention includes a roller electrode 222 which is rotatably mounted between a pair of conductive arms 223, 225 at their distal ends. The proximal ends of the arms 223, 225 are coupled to an electrode lead 226 and a mounting sleeve 227 in a conventional manner. The arms 223, 225 are preferably covered in an insulative material 228, 229, e.g., PTFE sheathing.

Figure 4:
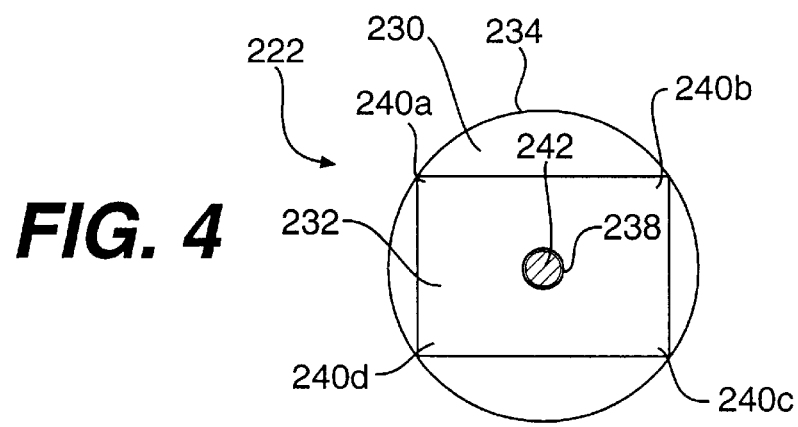
FIG. 4 is a cross-section across line 4—4 in FIG. 3.
Figure 5:
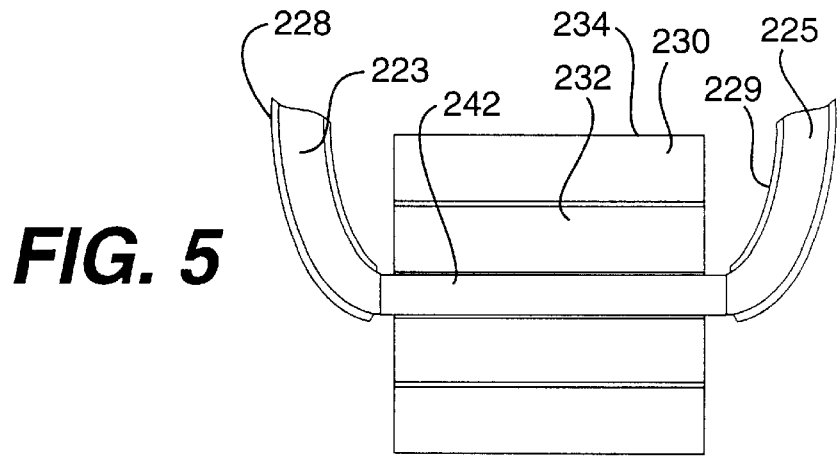
FIG. 5 is a cross-section across line 5—5 in FIG. 3.
Figure 6:
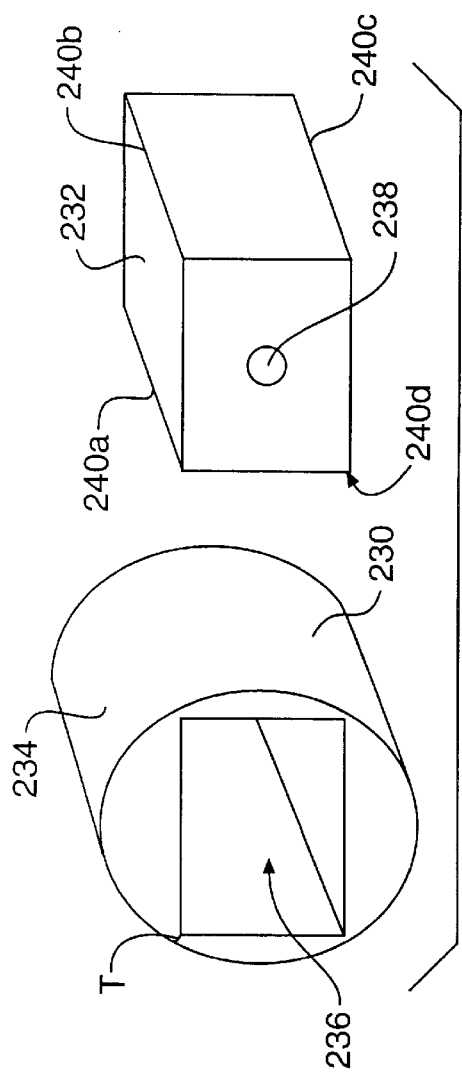
FIG. 6 is an exploded view of the roller electrode shown in FIG. 3.

Turning to FIGS. 4 through 6, the roller electrode 222 according to a first embodiment of the invention includes a substantially cylindrical member 230 and an insert 232. The cylindrical member 230 is provided with a smooth outer surface 234 and a central bore 236 having a polygonal cross-section. The cylindrical member 230 is made of a conductive material, preferably stainless steel. The insert 232 has its own axial bore 238 and is preferably shaped to have the same polygonal cross-section as the central bore 236, such that the insert 232 fits snugly within the central bore 236 of the cylindrical member 230. Preferably the central bore 236 and the insert 232 have a rectangular cross-section such that the insert is provided with four corners 240a–d. The insert 232 is made of a conductive material which is different than the conductive material of the cylindrical member 230, and preferably has a higher conductivity than the cylindrical member. For example, when the cylindrical member is made from stainless steel, the insert is preferably made from copper or tungsten.

An axle wire 242 extends between the arms 223, 225 and through the axial bore 238 of the insert in order to mount the roller electrode 222 and provide a conductive path from the arms 223, 225 to the insert 232. The axial bore 238 has a diameter of approximately 0.020 inches and the axle wire 242 has a diameter of approximately 0.016 inches, thereby permitting the roller electrode to freely rotate about the axle wire 242. The outer diameter of the cylindrical member 230 is preferably approximately 0.120 inches, while the distance T (see FIG. 6) from the corners 240a–d of the insert 232 to the outer surface 234 is preferably approximately 0.005 inches.

It will be appreciated that the corners 240a–d of the insert 232 focus the cautery energy through the cylindrical member 230 to provide high heat zones for enhanced tissue vaporization. In addition, the smooth outer surface 234 of the cylindrical member 230 in combination with the cautery focusing corners 240a–d of the insert 232 has been shown to minimize tissue accumulation on the surface of the roller electrode 222 while offering a relatively large surface area for cauterization.

Figure 7:
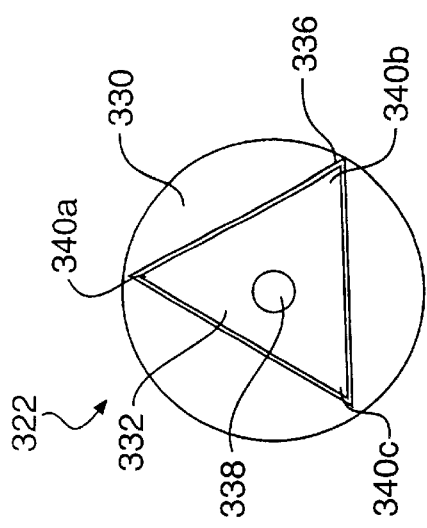
FIG. 7 is a view similar to FIG. 4 of a second embodiment of the invention.

Turning now to FIG. 7, a second embodiment of the invention is shown which is substantially similar to the first embodiment (with like parts having numbers incremented by 100). The electrode 322 includes a conductive cylindrical member 330 and a conductive insert 332. The cylindrical member 330 has a central bore 336 having a triangular cross-section. The insert 332 is triangular and has three corners 340a, 340b, 340c and an axial bore 338, and is shaped to fit snugly within the central bore 336 of the cylindrical member 330.

Figure 8:
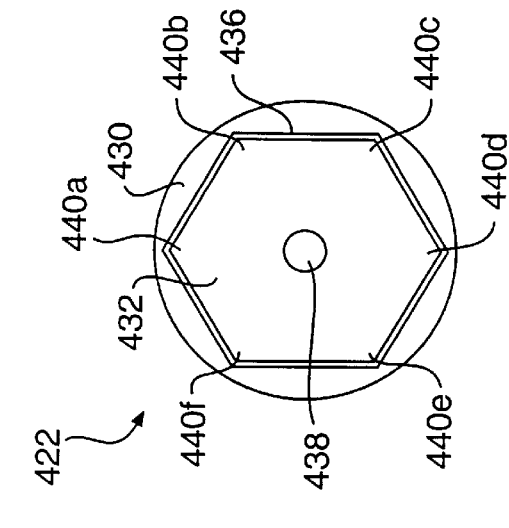
FIG. 8 is a view similar to FIG. 4 of a third embodiment of the invention.

Referring to FIG. 8, a third embodiment, substantially similar to the first embodiment (with like parts having numbers incremented by 200), is shown. The electrode 422 includes a conductive cylindrical member 430 and a conductive insert 432. The cylindrical member 430 has a central bore 436 having a hexagonal cross-section. The insert 432 has six corners 440a–f and an axial bore 438 and is shaped to fit snugly within the central bore 436 of the cylindrical member 430.

Figure 9:
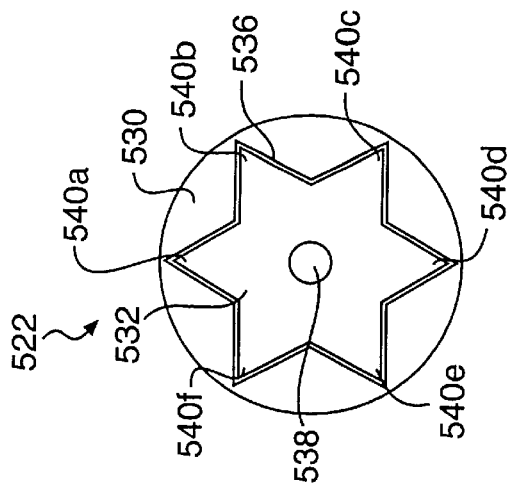
FIG. 9 is a view similar to FIG. 4 of a fourth embodiment of the invention.

Turning now to FIG. 9, a fourth embodiment, substantially similar to the first embodiment (with like parts having numbers incremented by 300), is shown. The electrode 522 includes a conductive cylindrical member 530 and a conductive insert 532. The cylindrical member 530 has a central bore 536 having a star-shaped cross-section. The insert 532 has six acute angled corners 440a–f and an axial bore 538 and is shaped to fit snugly within the central bore 536 of the cylindrical member 530.

Figure 10:
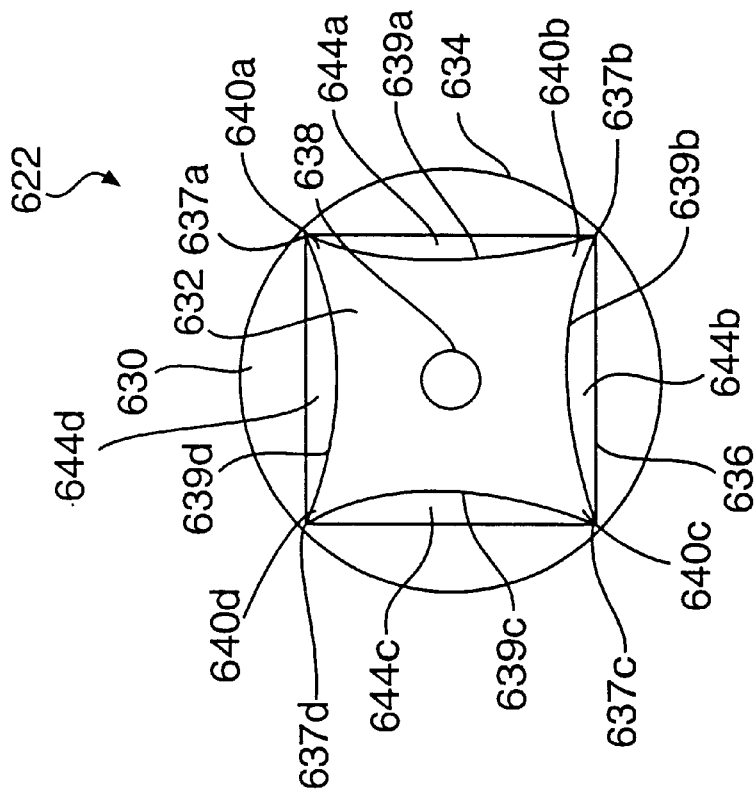
FIG. 10 is a view similar to FIG. 4 of a fifth embodiment of the invention.

Referring now to FIG. 10, a fifth embodiment, substantially similar to the first embodiment (with like parts having numbers incremented by 400), is shown. The electrode 622 includes a conductive cylindrical member 630 and a conductive insert 632. The cylindrical member has an outside surface 634, a central bore 636 having a rectangular cross-section, and four corners 637a–d. The insert 632 includes an axial bore 638 and has four concave sides 639a–d which define four corners 640a–d. The four corners 640a–d of the insert 632 fit snugly within the four corners 637a–d of the central bore 636 of the cylindrical member 630. Insulative air gaps 644a–d are formed between the concave sides 639a–d and the cylindrical member 630. The materials of the cylindrical member 630 and the insert 632 may be the same or different. It will be appreciated that when the insert 632 is made of the same material as the cylindrical member 630, the concave sides 639a–d and air gaps 644a–d restrict contact between the insert 632 and the cylindrical member 630 to substantially point contact at the corners 637a–d, 640a–d. As a result of the substantially point contact, the cautery current is focused into high heat zones on the outside surface 634 of the cylindrical member 630.

Figure 11:
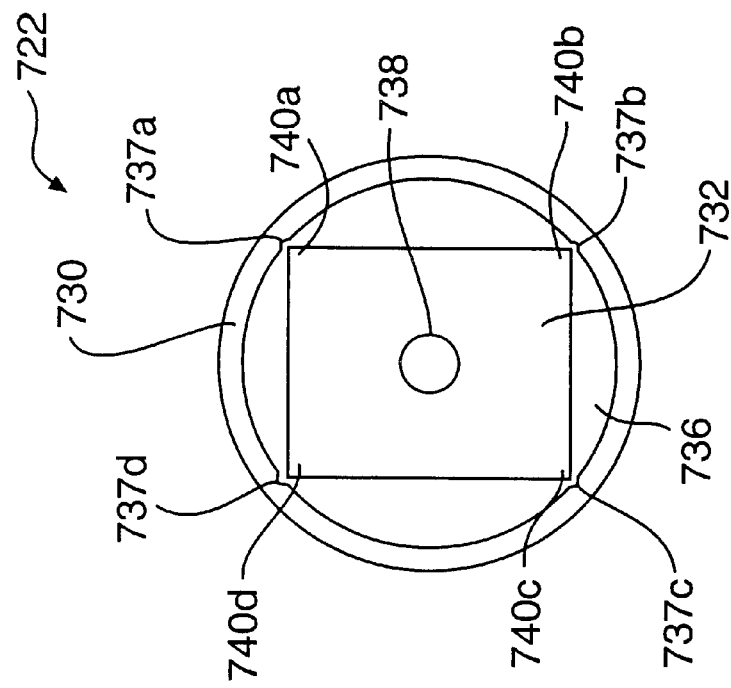
FIG. 11 is a view similar to FIG. 4 of a sixth embodiment of the invention.

Turning to FIG. 11, a sixth embodiment, substantially similar to the first embodiment (with like parts have numbers incremented by 500), is shown. The electrode 722 includes a conductive cylindrical member 730 and a conductive insert 732. The cylindrical member 730 has a central bore 736 having a circular cross-section. The insert 732 has a plurality of corners 740a–d and an axial bore 738 and is shaped to fit snugly within the central bore 736 of the cylindrical member 730. The central bore 736 of the cylindrical member 730 may have a plurality of notches 737*a–d* into which the corners 740*a–d* of the insert 732 engage to prevent the insert from rotating relative to the cylindrical member 730. The same or different materials may be used for the cylindrical member 730 and the insert 732.

Figure 12:
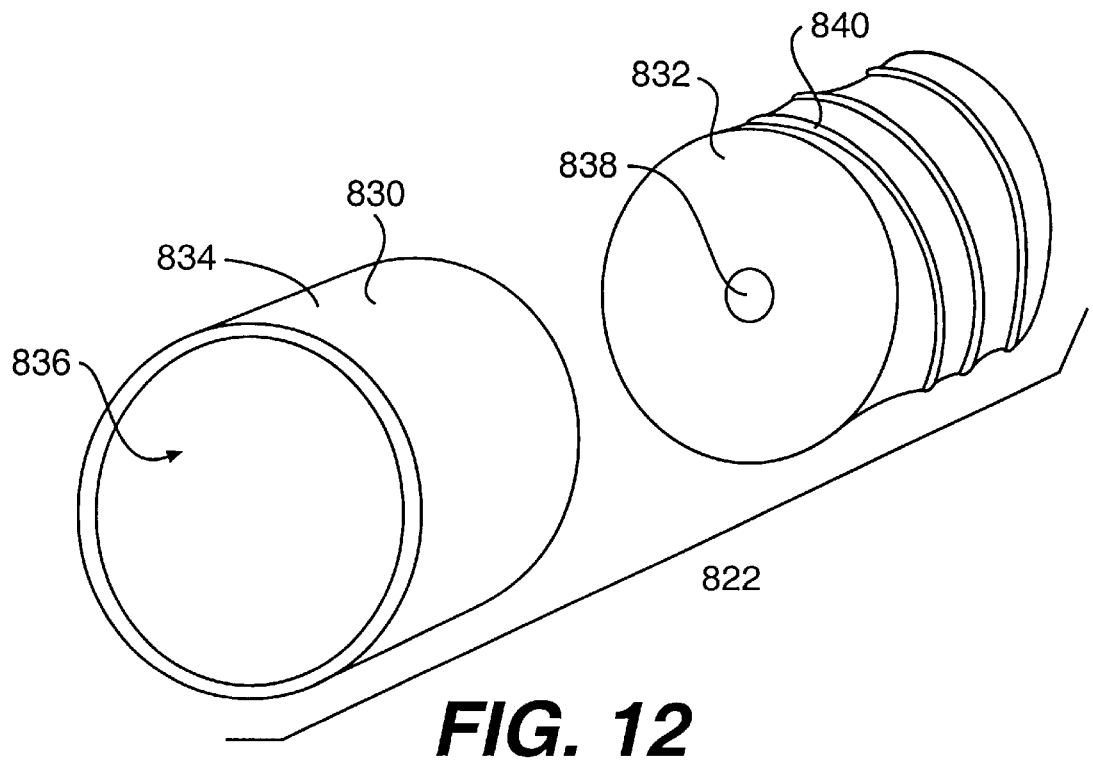
FIG. 12 is an exploded view of a seventh embodiment of a roller electrode.

Referring to FIG. 12, a seventh embodiment of the invention is shown. The electrode 822 includes conductive substantially cylindrical member 830 and a conductive substantially cylindrical insert 832. The cylindrical member 830 has a central bore 836 having a circular cross-section. The insert 832 has a raised helical ridge (or thread) 840 and an axial bore 838. The insert is sized and shaped to fit snugly within the central bore 836 of the cylindrical member 830. The central bore 836 of the cylindrical member 830 may further be threaded to receive the insert. The raised helical ridge focuses the cautery current on the outer surface 834 of the cylindrical member 830 at the locations directly above the raised ridge 840.

Figure 13:
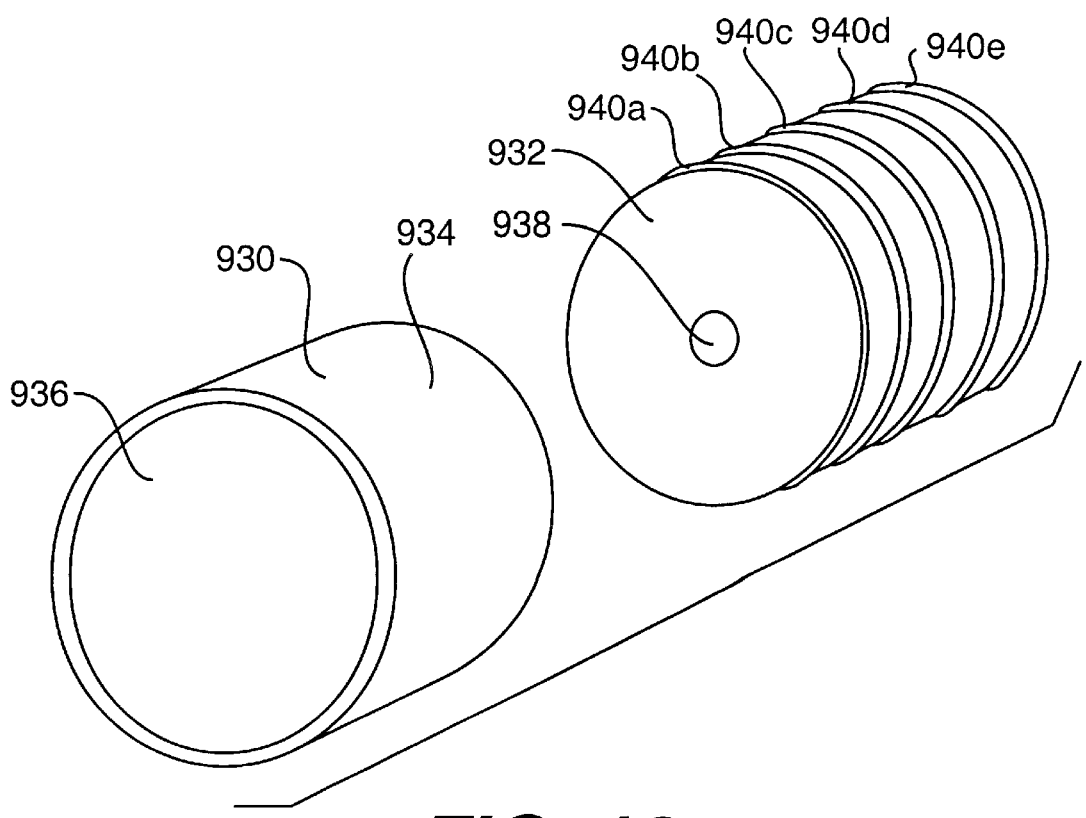
FIG. 13 is an exploded view of an eighth embodiment of a roller electrode.

Turning to FIG. 13, an eighth embodiment of the invention is shown. The electrode 922 includes conductive substantially cylindrical member 930 and a conductive substantially cylindrical insert 932. The cylindrical member 930 has a central bore 936 having a circular cross-section. The insert 932 has a plurality of raised circumfertial ridges 940*a–e* and an axial bore 938. The insert 932 is sized to fit snugly within the central bore 936 of the cylindrical member 930. The raised ridges 940*a–e* focus the cautery current on the outer surface 934 of the cylindrical member 930 at the locations directly above the raised ridges 940*a–e*.

There have been described and illustrated herein several embodiments of electrocautery probes for use with a resectoscope. While particular embodiments of the invention have been described, it is not intended that the invention be limited thereto, as it is intended that the invention be as broad in scope as the art will allow and that the specification be read likewise. Thus, while particular dimensions and materials have been disclosed, it will be appreciated that other dimensions and materials could be utilized. Also, while a number of cross-sections of the insert and the bore have been illustrated, it will be appreciated that the cross-sections of the insert and the bore may define any polygonal or other shape having corners. Moreover, while particular configurations have been disclosed in reference to features of the cautery probe carrying the electrode, it will be appreciated that other configurations of a cautery probe could be used with the provided electrodes. Furthermore, while the probes and electrodes have been disclosed as having particular utility in conjunction with a resectoscope, it will be understood that the cautery probes and electrodes disclosed herein can be used in other surgical procedures without requiring a resectoscope. It will therefore be appreciated by those skilled in the art that yet other modifications could be made to the provided invention without deviating from its spirit and scope as so claimed.

We claim:

1. A roller electrode for use in an electrocautery probe having at least one arm, said electrode comprising:
 a) a substantially cylindrical member defining a central bore, and having an outer surface and a first conductivity; and
 b) an insert having a plurality of corners and a second conductivity, said insert provided in said central bore in electrical communication with said cylindrical member.

2. A roller electrode according to claim 1, wherein:
 said first conductivity and said second conductivity are different.

3. A roller electrode according to claim 2, wherein:
 said second conductivity is greater than said first conductivity.

4. A roller electrode according to claim 1, wherein
 said insert is provided with an axial bore upon which said electrode is rotatably mounted.

5. A roller electrode according to claim 1, wherein:
 said central bore has a polygonal cross-section, and said insert has a cross-section substantially the same as said central bore.

6. A roller electrode according to claim 5, wherein:
 said central bore has a rectangular cross-section, and said insert has a cross-section substantially the same as said central bore.

7. A roller electrode according to claim 1, wherein:
 said cylindrical member is made of stainless steel.

8. A roller electrode according to claim 1, wherein:
 said insert is made of one of copper and tungsten.

9. A roller electrode according to claim 1, wherein:
 the distance from at least one of said plurality of corners to said outer surface is approximately 0.005 inches.

10. A roller electrode according to claim 1, wherein:
 said substantially cylindrical member has an outer diameter of approximately 0.120 inches.

11. A roller electrode according to claim 1, wherein:
 said insert contacts said cylindrical member only at said plurality of corners.

12. A roller electrode according to claim 11, wherein:
 said central bore is provided with a plurality of notches for engaging said plurality of corners.

13. An electrocautery probe, comprising:
 a) at least one conductive arm having proximal and distal ends;
 b) an electrode lead coupled to said proximal end of said at least one conductive arm and extending proximally therefrom; and
 c) a roller electrode mounted at said distal end of said at least one conductive arm, said roller electrode including:
  i) a substantially cylindrical member having a central bore, and outer surface, and a first conductivity, and
  ii) an insert having a plurality of corners and a second conductivity, said insert provided in said central bore in electrical communication with said cylindrical member.

14. An electrocautery probe according to claim 13, wherein:
 said first conductivity and said second conductivity are different.

15. An electrocautery probe according to claim 13, wherein:
 said insert is provided with an axial bore upon which said electrode is rotatably mounted.

16. An electrocautery probe according to claim 13, wherein:
 said central bore defines a polygonal cross-section, and said insert defines a cross section substantially the same as said central bore.

17. An electrocautery probe according to claim 13, wherein:
 said cylindrical member is made of stainless steel.

18. An electrocautery probe according to claim 13, wherein:
 said insert is made of one of copper and tungsten.

19. An electrocautery probe according to claim 13, wherein:
said second conductivity is greater than said first conductivity.

20. An electrocautery probe according to claim 13, wherein:
the distance from at least one of said plurality of corners to said outer surface is approximately .005 inches.

21. An electrocautery probe according to claim 13, wherein:
said insert contacts said cylindrical member only at said plurality of corners.

22. An electrocautery probe according to claim 21, wherein:
said central bore is provided with a plurality of notches for engaging said plurality of corners.

23. An electrocautery probe, comprising:
a) at least one conductive arm having proximal and distal ends;
b) an electrode lead coupled to said proximal end of said at least one conductive arm and extending proximally therefrom; and
c) a roller electrode mounted at said distal end of said at least one conductive arm, said roller electrode including:
   i) a substantially cylindrical member having a central bore, an outer surface, and a first conductivity, and
   ii) a substantially cylindrical insert having a plurality of grooves defining at least one raised ridge circumscribing said insert and a second conductivity, said insert provided in said central bore in electrical communication with said cylindrical member.

24. An electrocautery probe according to claim 23, wherein:
said at least one raised ridge circumscribes the circumference of said insert.

25. An electrocautery probe, comprising:
a) at least one conductive arm having proximal and distal ends;
b) an electrode lead coupled to said proximal end of said at least one conductive arm and extending proximally therefrom; and
c) a roller electrode mounted at said distal end of said at least one conductive arm, said roller electrode including:
   i) a substantially cylindrical member having a central bore, an outer surface, and a first conductivity, and
   ii) a substantially cylindrical insert having a helical groove defining a raised ridge helically circumscribing said insert and a second conductivity, said insert provided in said central bore in electrical communication with said cylindrical member.

* * * * *